(12) United States Patent
Ooms et al.

(10) Patent No.: US 6,555,703 B2
(45) Date of Patent: Apr. 29, 2003

(54) PROCESS FOR THE PREPARATION OF CARBOXYLIC ACID BENZYL ESTERS

(75) Inventors: Pieter Ooms, Krefeld (DE); Bernd-Ulrich Schenke, Bottrop (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/945,425

(22) Filed: Aug. 31, 2001

(65) Prior Publication Data

US 2002/0137966 A1 Sep. 26, 2002

(30) Foreign Application Priority Data

Sep. 4, 2000 (DE) .......................... 100 43 431

(51) Int. Cl.⁷ .................. C07C 67/24; C07C 205/00; C07C 69/76; C07C 67/30; C07C 67/00
(52) U.S. Cl. .................. 560/240; 560/20; 560/106; 560/203; 560/204
(58) Field of Search .................. 560/20, 106, 203, 560/204, 240

(56) References Cited

U.S. PATENT DOCUMENTS 2,030,835 A * 2/1936 Cox et al.

FOREIGN PATENT DOCUMENTS

| DE | 286 577 | 1/1991 |
|---|---|---|
| GB | 1 581 515 | 12/1980 |

OTHER PUBLICATIONS

Izumi et al, Acidic Salts of Heteropolyacids as Solid Acid Catalysts for Liquid–phase Organic Reactions, 1994, Studies in Surface Science and Catalysis, 90, pp. 1–8.*

Chem. Eng. Commun. vol. 100, (month unavailable) 1991, pp. 135–147, Ten–Tsai Wang, Ting–Chia Huang, Benzyl Acetate from Phase Transfer Catalyzed Acetate Displacement of Benzyl Chloride.

* cited by examiner

Primary Examiner—Johann Richter
Assistant Examiner—Paul A. Zucker
(74) Attorney, Agent, or Firm—Godfried R. Akorli; Diderico van Eyl

(57) ABSTRACT

The invention relates to a process for forming a carboxylic benzyl ester comprising reacting a dibenzyl ether with a carboxylic acid in the presence of a heteropolyacid and forming a carboxylic acid benzyl ester.

18 Claims, No Drawings

PROCESS FOR THE PREPARATION OF CARBOXYLIC ACID BENZYL ESTERS

BACKGROUND

The invention relates to a process for the preparation of carboxylic acid benzyl esters from dibenzyl ethers.

Benzyl acetate, the main component of jasmin oil, is an important fragrance for the preparation of scent compositions and starting material for the preparation of fruit ethers.

The preparation of benzyl acetate has already been widely reported. Thus, for example, the preparation of benzyl acetate by reacting benzyl alcohol with acetic acid has been known for a long time. Benzyl acetate can also be prepared by reacting benzyl chloride with alkali metal acetates, optionally in the presence of phase transfer reagents (Wang et al., Chem. Eng. Commun. 100, (1991), 135–147). A disadvantage is the formation of salts which have to be disposed of and thus reduce the costefficiency of this process.

DD-A5-286 577 describes the preparation of benzyl acetate by reacting dibenzyl ether with acetic anhydride. Disadvantages are the drastic reaction conditions (300° C./20 MPa) and the only moderate yields.

The object of the invention was therefore to provide a process for the preparation of dicarboxylic acid benzyl esters starting from dibenzyl ethers, which can be carried out under mild reaction conditions and leads to good yields.

Surprisingly, we have now found a process for the preparation of carboxylic acid benzyl esters and dibenzyl ethers which is characterized in that dibenzyl ethers are reacted with carboxylic acids in the presence of heteropolyacids as catalysts.

SUMMARY

The invention relates to a process comprising reacting a dibenzyl ether with a carboxylic acid in the presence of a heteropolyacid and forming a carboxylic acid benzyl ester. These and other features, aspects, and advantages of the present invention will become better understood with reference to the following description and appended claims.

DESCRIPTION

The invention relates to a process comprising reacting a dibenzyl ether with a carboxylic acid in the presence of a heteropolyacid and forming a carboxylic acid benzyl ester.

The dibenzyl ether used in the process according to the invention is an unsubstituted or substituted dibenzyl ether which can, for example, carry one or more substituents from the series branched or straight $C_1$–$C_6$-alkyl, $C_1$–$C_6$-alkoxy, CN, CO($C_1$–$C_6$)-alkyl, $NO_2$ or halogen. Preferred substituents are methyl, methoxy or chlorine. Particular preference is given to using unsubstituted dibenzyl ether.

In the process according to the invention, dibenzyl ethers or dibenzyl ether/benzyl alcohol mixtures, as are produced, for example, during the preparation of benzyl alcohol from benzyl chloride, can be used. The content of dibenzyl ether in dibenzyl ether/benzyl alcohol mixtures may, for example, be from about 50 to about 100% by weight, preferably from about 60 to about 100% by weight, particularly preferably from about 70 to about 100% by weight.

The carboxylic acids used in the process according to the invention are straight-chain or branched alkyl-, aryl- or aralkylcarboxylic acids which are saturated or unsaturated and contain 1 to 50 carbon atoms, preferably 2 to 30 carbon atoms, particularly preferably 2 to 10 carbon atoms. In the process according to the invention, it is possible to use acids such as formic acid, acetic acid, propionic acid, butyric acid, isobutyric acid, valeric acid, isovaleric acid, caproic acid, caprylic acid, lauric acid, myristic acid, stearic acid, oleic acid, acrylic acid, cinnamic acid, phenylacetic acid, benzoic acid or salicylic acid. Very particularly preferred carboxylic acids are acetic acid and propionic acid.

The process according to the invention is preferably carried out with removal of water that forms during the process. It is appropriate to remove the water by distillation or by passing through an inert gas such as nitrogen. To remove the water formed, preference is given to using dehydrating agents such as zeolites, aluminium oxides or clay earths. Particular preference is given to removing the water formed by carrying out the reaction in the presence of the corresponding anhydride of the carboxylic acid used as dehydrating agent. Very particularly preferred anhydrides are acetic anhydride and propionic anhydride.

In the process according to the invention, from about 2 to about 50 equivalents of carboxylic acid, preferably from about 3 to about 30 equivalents, particularly preferably from about 4 to about 20 equivalents, based on dibenzyl ether, are used.

If the process according to the invention is carried out in the presence of the corresponding anhydride of the carboxylic acid used, then from about 0.1 to about 10 equivalents of anhydride, preferably from about 0.5 to about 7.5 equivalents, particularly preferably from about 1 to about 5 equivalents, based on dibenzyl ether, are preferably used. Since one molecule of anhydride used reacts with the uptake of water to give 2 molecules of carboxylic acid, it is possible to use smaller amounts of carboxylic acid in the process according to the invention. From about 1 to about 25 equivalents of carboxylic acid, preferably from about 1.5 to about 15 equivalents, particularly preferably from about 2 to about 10 equivalents of carboxylic acid, based on dibenzyl ether, are then preferably used.

In the process according to the invention, the heteropolyacids used are preferably those of the formula (I)

$$A_a X_b M_c O_d \qquad (I)$$

in which

A represents protons and/or metal cations

X is P, Si, B, Ge, As, I, Se or Te

M is W, Mo, V or Cr a is 3, 4, 5 or 6, such that the heteropolyacids or salts thereof are electrically neutral b is 1 or 2 c is 12 or 18 and d is 40 or 62.

Suitable cations A which are to be mentioned are, for example, cations of the alkali metals, such as lithium, sodium, potassium, rubidium or caesium, or cations of the metals manganese, nickel, cobalt, copper or lanthanum or protons.

Preferred heteropolyacids are phosphomolybdic acid, phosphotungstic acid, phosphovanadic acid, silicomolybdic acid, silicotungstic acid, silicovanadic acid, and particularly preferred heteropolyacids are phosphomolybdic acid, phosphotungstic acid, silicomolybdic acid and silicotungstic acid.

Preferred heteropolyacids are also those of the Keggin type, i.e., compounds of the formula (I) in which b is 1, c is 12 and d is 40, and those of the Dawson type, i.e., compounds of the formula (I), in which b is 2, c is 18 and d is 62. Particularly preferred compounds are $A_3[PMo_{12}O_{40}]$, $A_3[PW_{12}O_{40}]$, $A_3[SiMo_{12}O_{40}]$ and $A_3[SiW_{12}O_{40}]$.

Methods for the preparation of the heteropolyacids are known and described, for example, in Römpp, Lexikon der Chemie volume 3, 10th edition, Stuttgart/New York 1997, p. 1741; Chemical Reviews 98, 1998, 1ff or Catal. Rev. Sci. Eng. 37, 1995, 311ff.

The heteropolyacids can also be used in the form of their hydrates. It is also possible to use mixtures of heteropolyacids in the process according to the invention.

In the process according to the invention, the heteropolyacids may be used or may be present as homogeneous catalysts or as heterogeneous catalysts. Whether the heteropolyacids are present as homogeneous or heterogeneous catalysts depends on the type and amount of the heteropolyacid used. Furthermore, the heteropolyacids can be used as heterogeneous catalysts applied to an inert support. Suitable support materials are, for example, activated carbon, silica gel, aluminium oxide, alumosilicates, such as zeolites, or phyllosilicates, clay earths, titanium oxides or zirconium oxides.

If supported heteropolyacids are used in the process according to the invention, then these are preferably used in dried form. The drying can be achieved by heat and/or reduced pressure. Furthermore, drying may take place by washing with hydrophilic liquids such as the carboxylic acid used in the process or the corresponding carboxylic anhydride, or by azeotropic distillation with organic solvents, e.g., toluene, xylene or methylene chloride.

The supported heteropolyacids can be used as powders or molded bodies, e.g., balls, cylinders, wads, hollow cylinders or rings. In this connection, the supported heteropolyacids can be used in the process according to the invention in suspended form or as a fixed bed catalyst.

If the optionally supported heteropolyacid is used in suspended form or if the heteropolyacid is present in homogeneous form, then it is preferably used in an amount of from about 0.1 to about 100% by weight, preferably from about 0.5 to about 90% by weight, particularly preferably from about 0.1 to about 80% by weight, based on dibenzyl ether. The process is preferably carried out with intensive thorough mixing of the reactants. Intensive thorough mixing can be achieved in various ways known to the person skilled in the art, for example, by stirrers, nozzles, baffles, static mixers, pumps, turbulent flows into narrow tubes or by ultrasound.

In a preferred embodiment of the process according to the invention, the optionally supported heteropolyacid is suspended in the carboxylic acid used, preferably in a mixture of carboxylic acid used and the corresponding carboxylic anhydride, or is mixed with said acid, and then dibenzyl ether is metered in. When the reaction is complete, the suspended optionally supported heteropolyacid can be separated off, for example, by filtration or centrifugation. If the heteropolyacid used is present in homogeneous form, then it is preferably neutralised by adding a base and the reaction product is isolated by subsequent distillation.

If the supported heteropolyacid is used as a fixed bed catalyst, then space velocities of from about 0.05 to about 5000 g of dibenzyl ether per liter of catalyst per hour, preferably of from about 0.1 to about 4000 g of dibenzyl ether per liter of catalyst per hour, particularly preferably about 1.0 to about 3000 g of dibenzyl ether per liter of catalyst per hour, are preferably used.

In a preferred embodiment of the process according to the invention, the supported heteropolyacid is in the form of a fixed bed catalyst and is preferably arranged as catalyst packing in a tube. The starting materials dibenzyl ether and carboxylic acid, preferably in a mixture with the corresponding carboxylic anhydride, can be brought into contact with the catalyst in cocurrent or countercurrent by flooding.

In a further preferred embodiment of the process according to the invention, this is carried out in the trickle phase and the supported heteropolyacid is in the form of a fixed bed catalyst. Preferably, the catalyst packing is situated in a vertical tubular reactor which preferably contains intermediate plates to better distribute the stream of liquid and to better wet the catalyst packing. The starting materials are preferably applied to the catalyst packing in cocurrent, for example, from the top downwards. At the end of the tube, the reaction products can be drawn off.

Both in the case of the presence of a heterogeneous suspended heteropolyacid, which is optionally supported, and also in the case of the fixed-bed process variant, the work-up can be carried out such that a water-immiscible solvent, preferably toluene, is added to the reaction products. Following removal of the organic phase, which comprises the crude carboxylic acid benzyl ester, it can be further purified, for example by distillation.

The process according to the invention can be carried out batchwise, semi-continuously or continuously.

The temperature at which the process according to the invention is carried out is preferably from about 15 to about 200° C., particularly preferably from about 25 to about 190° C., very particularly preferably from about 30 to about 180° C.

If the process according to the invention is carried out above about 115° C., it is necessary to work under increased pressure corresponding to the vapor pressure. The gauge pressure required is then at least equal to the vapor pressure of the reaction mixture. It may be up to about 50 bar, preferably up to about 25 bar.

Where appropriate, the process according to the invention can be carried out under a customary protective gas, e.g., nitrogen, helium or argon.

The process according to the invention gives carboxylic acid benzyl esters in good yields coupled with high conversion and good selectivity. The process according to the invention can be carried out easily without high expenditure on apparatus.

The invention is further described in the following illustrative examples in which all parts and percentages are by weight unless otherwise indicated.

EXAMPLES

Example 1

99.2 g (0.5 mol) of dibenzyl ether, 120.0 g (2.0 mol) of acetic acid and 0.5 g of phosphotungstic acid (Johnson Matthey) were heated in a flask with a baffle and a paddle stirrer with vigorous stirring (250 rpm) and under nitrogen at 120° C. After a reaction time of 5 h, the mixture was cooled rapidly, the organic phase was separated off following the addition of toluene and water, and analysed by gas chromatography.

The reaction mixture comprised benzyl acetate and dibenzyl ether in the ratio 58 to 19.

Example 2

Example 2 was carried out analogously to Example 1. 240.0 g (4.0 mol) of acetic acid were used and the reaction time was 3 h.

The reaction mixture comprised benzyl acetate and dibenzyl ether in the ratio 67 to 15.

Example 3

Example 3 was carried out analogously to Example 1. 600.0 g (10.0 mol) of acetic acid were used.

The reaction mixture comprised benzyl acetate and dibenzyl ether in the ratio 82 to 5.

Example 4

Example 4 was carried out analogously to Example 1. 300.0 g (5.0 mol) of acetic acid and 0.5 g of silicotungstic acid (Aldrich) were used, and the reaction time was 7 h.

The reaction mixture comprised benzyl acetate and dibenzyl ether in the ratio 81 to 4.

Example 5

Example 5 was carried out analogously to Example 1. 99.2 g (0.5 mol) of dibenzyl ether, 30.0 g (0.5 mol) of acetic acid, 51.1 g (0.5 mol) of acetic anhydride and 0.5 g of phosphotungstic acid (Johnson Matthey) were reacted at 100° C. The reaction time was 1 h.

The reaction mixture comprised benzyl acetate and dibenzyl ether in the ratio 80 to 1.

Example 6

Example 6 was carried out analogously to Example 5. 0.5 g of silicotungstic acid (Aldrich) were used.

The reaction mixture comprised benzyl acetate and dibenzyl ether in the ratio 81 to 1.

Example 7

Example 7 was carried out analogously to Example 5. 0.5 g of phosphomolybdic acid (Aldrich) was used, and the reaction time was 7 h.

The reaction mixture comprised benzyl acetate and dibenzyl ether in the ratio 50 to 29.

Example 8

Example 8 was carried out analogously to Example 5. 0.5 g of silicomolybdic acid (Aldrich) was used.

The reaction mixture comprised benzyl acetate and dibenzyl ether in the ratio 47 to 30.

Example 9

Example 9 was carried out analogously to Example 5. 0.1 g of phosphotungstic acid (Johnson Matthey) was used, the reaction was carried out at 23° C. and the reaction time was 3 h.

The reaction mixture comprised benzyl acetate and dibenzyl ether in the ratio 70 to 5.

Example 10

Example 10 was carried out analogously to Example 4. 79.3 g (0.4 mol) of dibenzyl ether and 21.6 g (0.2 mol) of benzyl alcohol were used and the reaction time was 5 h.

The reaction mixture comprised benzyl acetate and dibenzyl ether in the ratio 70 to 18.

Example 11

Example 11 was carried out analogously to Example 5. 3.0 g of a catalyst, prepared by applying 75 g of phosphotungstic acid (Johnson Matthey) to 1000 ml of aluminium oxide SPH 512 (Rhone-Poulenc), were used and the reaction time was 7 h.

The reaction mixture comprised benzyl acetate and dibenzyl ether in the ratio 62 to 19.

Example 12

Example 12 was carried out analogously to Example 5. 3.0 g of a catalyst, prepared by applying 75 g of phosphotungstic acid (Johnson Matthey) to 1000 ml of active carbon ROX 0.8 (Norit), were used and the reaction time was 1 h.

The reaction mixture comprised benzyl acetate and dibenzyl ether in the ratio 77 to 1.

Example 13

Example 13 was carried out analogously to Example 5. 37.0 g (0.5 mol) of propionic acid and 65.1 g (0.5 mol) of propionic anhydride were used and the reaction time was 1 h.

The reaction mixture comprised benzyl propionate and dibenzyl ether in the ratio 78 to 1.

Example 14 (Continuous Process)

In a reactor with 60 parts by volume of catalyst arranged as a fixed bed and prepared by applying 75 parts by weight of phosphotungstic acid (Johnson Matthey) to 1000 parts by volume of titanium oxide HSA (Norton), a mixture of 11.9 parts by weight/h of dibenzyl ether and 37.6 parts by weight/h of acetic acid was charged at the upper end of the reactor through the catalyst bed at a temperature of 100° C. The reaction mixture leaving the reactor comprised benzyl acetate and dibenzyl ether in the ratio 63.5 to 21.2.

Space-time yield: 0.084 kg/1 h (based on the catalyst).

Although the present invention has been described in detail with reference to certain preferred versions thereof, other variations are possible. Therefore, the spirit and scope of the appended claims should not be limited to the description of the versions contained therein.

What is claimed is:

1. A process for forming a carboxylic benzyl ester comprising reacting a dibenzyl ether with a carboxylic acid in the presence of a heteropolyacid and forming a carboxylic acid benzyl ester.

2. The process according to claim 1, wherein the heteropolyacid is of the formula (I):

$$A_a X_b M_c O_d \qquad (I)$$

wherein

A represents protons, metal cations, or protons and metal cations,

X is P, Si, B, Ge, As, I, Se or Te,

M is W, Mo, V or Cr, a is 3, 4, 5 or 6, such that the heteropolyacids or salts thereof are electrically neutral, b is 1 or 2, c is 12 or 18, and d is 40 or 62.

3. The process according to claim 2, wherein A is a cation selected from the group consisting of hydrogen, lithium, sodium, potassium, rubidium, caesium, manganese, nickel, cobalt, copper and lanthanum.

4. The process according to claim 1, wherein the heteropolyacid is a component selected from the group consisting of phosphomolybdic acid, phosphotungstic acid, phosphovanadic acid, silicomolybdic acid, silicotungstic acid and silicovanadic acid.

5. The process according to claim 1, wherein the dibenzyl ether is an unsubstituted dibenzyl ether.

6. The process according to claim 1, wherein the dibenzyl ether is a substituted dibenzyl ether which carries one or more substituents selected from the group consisting of $C_1$–$C_6$-alkyl, $C_1$–$C_6$-alkoxy, CN, CO($C_1$–$C_6$-alkyl), $NO_2$ or halogen.

7. The process according to claim 1, wherein the dibenzyl ether is in a mixture with benzyl alcohol.

8. The process according to claim 1, wherein the carboxylic acid is present in an amount ranging from about 2 to about 50 equivalents, based on dibenzyl ether.

9. The process according to claim 1, wherein the reacting of the dibenzyl ether with the carboxylic acid is carried out with removal of water formed during the process.

10. The process according to claim 7, wherein water formed during the process is removed by distillation or by passing through an inert gas.

11. The process according to claim 1, wherein the reacting of the dibenzyl ether with the carboxylic acid is carried out in the presence of the corresponding anhydride of the carboxylic acid.

12. The process according to claim 11, wherein the anhydride is used in an amount ranging from about 0.1 to about 10 equivalents, based on dibenzyl ether.

13. The process according to claim 1, wherein the heteropolyacid is in an amount ranging from about 0.1 to about 100% by weight, based on dibenzyl ether.

14. The process according to claim 1, wherein the heteropolyacid is present in a supported form.

15. The process according to claim 14, wherein the supported heteropolyacid is present in suspended form within the reaction mixture.

16. The process according to claim 14, wherein the supported heteropolyacid is used as a fixed bed catalyst.

17. The process according to claim 16, wherein the dibenzyl ether has a space velocity ranging from about 0.05 g to about 5000 g of dibenzyl ether per liter of supported heterpolyacid per hour.

18. The process according to claim 1, wherein the reacting of the dibenzyl ether with the carboxylic acid is carried out at a temperature ranging from about 15 to about 200° C.

* * * * *